(12) United States Patent
Boese et al.

(10) Patent No.: US 8,165,839 B2
(45) Date of Patent: Apr. 24, 2012

(54) CALIBRATION OF AN INSTRUMENT LOCATION FACILITY WITH AN IMAGING APPARATUS

(75) Inventors: Jan Boese, Eckental (DE); Matthias John, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 539 days.

(21) Appl. No.: 12/378,003

(22) Filed: Feb. 10, 2009

(65) Prior Publication Data
US 2009/0205403 A1 Aug. 20, 2009

(30) Foreign Application Priority Data
Feb. 15, 2008 (DE) .......................... 10 2008 009 266

(51) Int. Cl.
*G01D 21/00* (2006.01)
*G06F 19/00* (2011.01)

(52) U.S. Cl. ............ 702/85; 73/1.79; 73/865.9; 702/94; 702/189; 708/105; 708/442

(58) Field of Classification Search .................. 73/1.01, 73/1.79, 432.1, 865.8, 865.9; 702/1, 85, 702/94, 95, 105, 127, 150, 152, 187, 189; 708/100, 105, 131, 160, 200, 204, 206, 442
See application file for complete search history.

(56) References Cited

U.S. PATENT DOCUMENTS

| | | | | |
|---|---|---|---|---|
| 5,829,444 A * | 11/1998 | Ferre et al. | ..................... | 128/897 |
| 6,050,724 A * | 4/2000 | Schmitz et al. | ................. | 378/205 |
| 6,052,611 A * | 4/2000 | Yanof et al. | .................... | 600/429 |
| 6,064,904 A * | 5/2000 | Yanof et al. | .................... | 600/414 |
| 6,165,181 A * | 12/2000 | Heilbrun et al. | ............... | 606/130 |
| 6,470,207 B1 * | 10/2002 | Simon et al. | ................... | 600/426 |
| 6,490,477 B1 * | 12/2002 | Zylka et al. | .................... | 600/429 |
| 6,533,455 B2 | 3/2003 | Graumann et al. | | |
| 6,856,827 B2 | 2/2005 | Seeket et al. | | |
| 6,923,768 B2 * | 8/2005 | Camus et al. | ................. | 600/463 |
| 2001/0053204 A1 | 12/2001 | Navab et al. | | |
| 2002/0044631 A1 * | 4/2002 | Graumann et al. | ........... | 378/205 |
| 2003/0018251 A1 | 1/2003 | Solomon | | |
| 2003/0088179 A1 * | 5/2003 | Seeley et al. | .................. | 600/424 |
| 2003/0220561 A1 * | 11/2003 | Camus et al. | ................. | 600/424 |
| 2004/0152974 A1 | 8/2004 | Solomon | | |
| 2007/0276227 A1 | 11/2007 | Boese et al. | | |

FOREIGN PATENT DOCUMENTS

| | | |
|---|---|---|
| DE | 10137914 A1 | 5/2002 |
| DE | 102006024425 A1 | 11/2007 |
| WO | WO 2007044792 A1 | 4/2007 |
| WO | WO 2007135609 A2 | 11/2007 |

OTHER PUBLICATIONS

Baratoff et al., "Tracking Devices", .hitl.washington.edu/scivw/EVE/I.D.1.b.TrackingDevices.html; Feb. 2, 2008; pp. 1-4.
Fischer et al., "Intensity based image registration with a guaranteed one-to-one point match", Methods of Information in Medicine, 2004, pp. 327-330, Schattauer Verlag, Stuttgart, 43.

* cited by examiner

*Primary Examiner* — Edward Cosimano

(57) ABSTRACT

A method is proposed for calibrating an instrument location facility with an imaging apparatus. The instrument location apparatus and the imaging apparatus are synchronized temporally with one another. According to such synchronization at least three points of the position of a medical instrument relative to a tracking coordinate system of the instrument location apparatus and/or relative to an image coordinate system of the imaging apparatus are measured simultaneously both by the instrument location apparatus and by the imaging apparatus. The instrument and/or the imaging apparatus are moved relative to one another between the measurements. The measured points parameterize a predetermined transformation rule for mapping the tracking coordinate system onto the image coordinate system.

12 Claims, 1 Drawing Sheet

CALIBRATION OF AN INSTRUMENT LOCATION FACILITY WITH AN IMAGING APPARATUS

CROSS REFERENCE TO RELATED APPLICATIONS

This application claims priority of German application No. 10 2008 009 266.5 filed Feb. 15, 2008, which is incorporated by reference herein in its entirety.

FIELD OF THE INVENTION

The invention relates to a method for calibrating an instrument location facility with an imaging apparatus, in particular for mapping a so-called tracking coordinate system of the location apparatus onto an image coordinate system of the imaging apparatus. The invention also relates to a facility configured to implement the method.

BACKGROUND OF THE INVENTION

A medical intervention, for example the ablation of diseased cardiac tissue to treat cardiac arrhythmia is generally carried out by means of a medical instrument—for example a catheter—inserted into the patient's body. During the treatment the treating physician then generally does not have direct sight of the instrument and the body region to be treated. Instead, in order to be able to carry out the treatment precisely the instrument is normally made visible within the patient's body by means of an imaging method. The imaging methods used for this purpose are in particular x-ray imaging methods. The instrument can then be tracked for example in an x-ray image of the patient.

Additionally or alternatively an instrument location facility (also referred to as a tracking system) is frequently deployed to determine instrument position. Such a tracking system captures the position of the instrument in space by means of an optical, acoustic, electromagnetic or impedance-based method. To this end detection points defined on the instrument are frequently provided, which can be detected by the tracking system.

Imaging apparatuses with real-time resolution, e.g. x-ray fluoroscopy devices, generally only provide a two-dimensional but therefore relatively precise image of the instrument. With a tracking system however the spatial position of the instrument can be determined continuously in real time, although generally only locally; there is no overview of the entire object or environment. Also the position determination of the tracking system is frequently inaccurate. In particular a tracking system often shows the instrument position in a distorted manner.

In order to be able to make better use of the respective advantages of imaging and instrument tracking, the coordinate systems of the imaging apparatus and the tracking system are superimposed, so that a corresponding point in the image coordinate system can be determined for each point in the tracking coordinate system. For example the position information from the tracking system can then be used to display the medical instrument in a three-dimensional x-ray image produced beforehand by imaging, in particular a computed tomogram or angiogram, and to navigate it in this virtual 3D image of the patient.

The superimposition or mapping of the tracking coordinate system with the image coordinate system is also referred to as registration. To carry out such registration a so-called calibration phantom is generally used, which contains a large number of detectable marking points, whose relative positions in respect of one another are known. The calibration phantom is in a fixed position in space, for example under a patient table, and it determines the location of the marking points thus established both by means of imaging and also by means of the tracking system. The captured coordinates of the marking points in the tracking coordinate system and in the image coordinate system are then used to determine a transformation rule, which maps the tracking coordinate system onto the image coordinate system.

However such a registration is relatively complex to carry out and sometimes disrupts the ongoing operation of the associated medical facility.

SUMMARY OF THE INVENTION

The object of the invention is to specify a method for calibrating an instrument location apparatus with an imaging apparatus, which can be implemented quickly and in particular simply during the ongoing operation of a medical facility comprising such apparatuses. It is also the object of the invention to specify a facility that is particularly suitable for implementing the method.

In respect of the method this object is achieved according to the invention by the features of the first embodiment. According to this provision is made to synchronize the instrument location apparatus, referred to below as the tracking system, and the imaging apparatus temporally with one another, so that it is ensured that both apparatuses operate on a common time scale.

According to such synchronization at least three measurements are taken simultaneously of the position of a medical instrument using both the tracking system and the imaging apparatus in accordance with the method. The instrument and/or the imaging apparatus is/are moved relative to one another between measurements. Therefore during the course of the measurements the instrument can be moved while the imaging apparatus remains fixed. Or the imaging apparatus is moved in relation to the fixed instrument. Or both the instrument and the imaging apparatus are moved, so that the relative positioning of the instrument in respect of the imaging apparatus in space changes. As a result of each of these measurements therefore a position of the instrument is established both in a tracking coordinate system assigned to the tracking system and in an image coordinate system assigned to the imaging apparatus.

The established instrument positions are then used to carry out registration, by parameterizing a predetermined transformation rule so that the tracking coordinate system is mapped onto the image coordinate system. Parameterization here is understood to be the determination of specific values for the parameters of the transformation rule that are initially predetermined in an abstract manner.

The imaging apparatus is in particular an x-ray device, preferably a so-called C-arm x-ray device. The tracking system detects one or a number of defined detection points on the instrument to be located. These detection points are either passive markings or transmitters or receivers of the tracking system.

According to the proposed method it is advantageously not necessary to deploy a calibration phantom or similar additional devices to carry out the registration. Instead only the instrument used anyway for treatment purposes is required for registration. Furthermore registration according to the method described above can also take place during normal medical treatment, without the treating physician having to take any measures. During treatment the instrument to be located is generally always subject to certain movement, so the different instrument positions required to parameterize the transformation rule are automatically assumed. In particular if the instrument is a hand-held instrument, the instrument is generally already moved sufficiently by the motor activity of the user, therefore unconsciously on the part of the user.

Because according to the method the coordinate systems are registered on the basis of the moving medical instrument, it is also possible to refresh or check registration at any time, even during treatment.

To achieve different instrument positions in the image coordinate system, in an expedient embodiment of the method the orientation of the image axis in space is changed in addition or as an alternative to the movement of the instrument in ambient space.

In order to be able to collect as many different instrument positions as possible in the shortest possible time, in one variant of the method provision is made to determine the positions of a number of instruments and/or optionally a number of defined detection points on an instrument during the course of the measurements.

In the case of an imaging apparatus with a number of image axes angled in relation to one another, for example a so-called biplanar x-ray system, provision is made for the same purpose in a further variant of the method for the position of the instrument to be determined simultaneously in the image coordinate systems assigned respectively to these image axes.

In particular when using an x-ray device as an imaging apparatus the image coordinate system is in particular a two-dimensional coordinate system, which describes an image area arranged perpendicular to an image axis in space. In the case of an x-ray device the image axis is the central beam of the x-ray field emitted from the x-ray source onto the x-ray detector of the device and the image area is the detector area.

In an advantageous embodiment of the method a combination of affine mapping and projection is used as the transformation rule. According to the mathematical definition of the term, affine mapping is understood to be mapping between the vector spaces spanned by the image coordinate system and/or the tracking coordinate system, which preserves collinearity and ratios of distances of parallel routes. A combination of one or a number of translations and rotations, and optionally scalings and shears, is used in particular as affine mapping.

In one advantageous method variant the transformation rule is given as a matrix equation of the type $$p_{PCS} = M_p \cdot T \cdot p_{TCS}$$

Here
  $p_{PCS}$ is an image point corresponding to a measured instrument position in coordinates of the image coordinate system,
  $p_{TCS}$ is a point corresponding to this measured instrument position in coordinates of the tracking coordinate system,
  T is a transformation matrix mapping the tracking coordinate system onto a spatial coordinate system of the imaging apparatus, and
  $M_p$ is a projection matrix mapping the spatial coordinate system onto the image coordinate system as a function of the location of the image axis.

When using an x-ray device as an imaging apparatus the image coordinate system is in particular
  a two-dimensional Cartesian coordinate system: $p_{PCS} = (u_{PCS}, v_{PCS})^T$,
  the spatial coordinate system of the imaging apparatus is a three-dimensional Cartesian coordinate system: $p_{RCS} = (x_{RCS}, y_{RCS}, z_{RCS})^T$, and
  the tracking coordinate system is likewise a three-dimensional Cartesian coordinate system: $p_{TCS} = (x_{TCS}, y_{TCS}, z_{TCS})^T$.

Mathematical column vectors are shown here with parenthesis expressions of the type $(\ldots)^T$. For simplified mathematical processing the points $p_{PCS}$ and $p_{TCS}$ in EQU 1 are optionally written in the form of so-called homogeneous coordinates and in this context are extended respectively by a (formal) dimension.

The parameters of the transformation matrix are preferably determined approximately using an iteration method. Alternatively the parameters of the transformation matrix can be determined by mathematically analytical resolution of the transformation rule for the measured instrument positions, in particular by resolution of the transformation rule as a linear equation system.

Distortion of the tracking coordinate system is also advantageously identified and taken into account during the course of the registration method, with distortion thus being eliminated from the tracking coordinate system. To this end provision is made for parameterizing a non-rigid transformation rule in a minimization method. A transformation is referred to as non-rigid, if it cannot be traced back exclusively to rotations and translations.

In one expedient embodiment a transformation rule of the type $$\Sigma M(T(p_{TCS}), s_p) + \alpha \cdot S(T)$$

is used here. Here
  $p_{TCS}$ is again a point corresponding to a measured instrument position in coordinates of the tracking coordinate system,
  T is a transformation function mapping the tracking coordinate system onto the spatial coordinate system of the imaging apparatus,
  $s_p$ is an image beam, which is assigned to an image point $p_{PCS}$ corresponding to the measured instrument position in coordinates of the image coordinate system,
  M is a measure indicating the distance of the point $T(p_{TCS})$ from the image beam $s_p$,
  $\alpha$ is a weighting factor, and
  S is a measure of the degree of distortion of the mapping function T.

Preferably either the imaging apparatus or the tracking system is used as a signal generator for the capturing of the instrument positions by both apparatuses. In this embodiment therefore the signal-generating apparatus triggers the respective other apparatus, so that simultaneous position capturing is ensured. Alternatively provision can be made for both apparatuses to capture the instrument position in an essentially continuous manner, with each measurement being provided with a synchronized time stamp. The time stamp can then be used to assign simultaneous position measurements of both apparatuses to one another retrospectively.

Position determination is expediently carried out automatically in the context of the imaging apparatus by image processing software, which is able to identify certain defined detection points on the instrument in an image, in particular an x-ray image. In one alternative embodiment of the method it is also possible to carry out position determination in the image manually. For example the position of the instrument in the image is then marked with the aid of a computer mouse.

In one expedient embodiment of the method an electromagnetic tracking system is used. The instrument here comprises a coil arrangement arranged in the detection point provided, said coil arrangement being used to measure the strength of magnetic fields generated by external coils. The measured magnetic field is used to calculate the position of the instrument.

In one advantageous alternative embodiment an impedance-based tracking system is used. For example three pairs of external electrodes, arranged approximately orthogonally, are attached to the skin of the patient, with defined alternating current voltages being applied to them one after the other. The instrument is provided with one or a number of measuring electrodes arranged at the detection point. The voltage present at the instrument can be used to determine the impedance between the instrument and the electrodes, from which it is possible to determine the position of the instrument approximately.

In another alternative embodiment of the method an acoustic tracking system is used, with the position of the instrument being determined according to the "bat principle" using sound waves, in particular ultrasound waves. In the context of such a tracking system the instrument is in particular passive, in other words is not itself provided with sound generators or sound detectors.

A mechanical tracking system or an optical tracking system can also be used in the context of the method.

In respect of the facility the above-mentioned object is achieved according to the invention by the features of the second embodiment. According to this the facility comprises an instrument location apparatus (i.e. a tracking system), an imaging apparatus and a control unit activating these apparatuses. The control unit here comprises a registration module configured with appropriate circuits and/or programs to implement the method described above. The control unit is preferably a data processing system, the registration module preferably a software module implemented on this data processing system. However the registration module can also be formed wholly or partially from hardware components.

BRIEF DESCRIPTION OF THE DRAWINGS

An exemplary embodiment of the invention is described in more detail below with reference to a drawing, in which.

Corresponding parts and variables are shown with the same reference characters in all the figures.

DETAILED DESCRIPTION OF THE INVENTION

Figure 1:
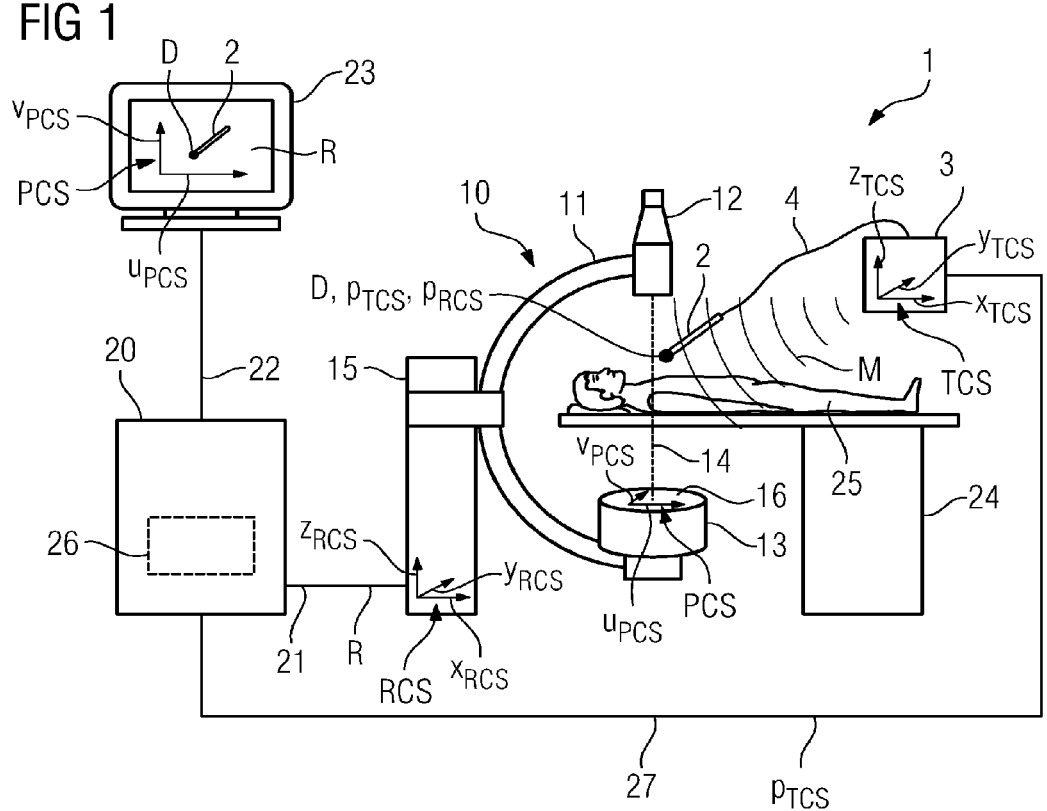
FIG. 1 shows a schematic diagram of a medical facility for locating and visualizing a medical instrument with a tracking system, a C-arm x-ray device and a control unit.

The facility 1 shown in FIG. 1 is used to locate and visualize a medical instrument 2 (only shown roughly in FIG. 1), which is for example a catheter.

To this end the facility 1 comprises an instrument location apparatus (referred to below as a tracking system 3), which is configured to determine the position of a defined detection point D on the instrument 2 as a point $p_{TCS}$ in a three-dimensional tracking coordinate system TCS with coordinates $x_{TCS}$, $y_{TCS}$, $z_{TCS}$. The detection point D is for example the tip of the instrument 2.

In the example shown the tracking system 3 is based on an electromagnetic detection principle. A spatially inhomogeneous magnetic field M is produced here by a transmitter (not shown) of the tracking system 3. The tracking system 3 also comprises three measuring coils, which are arranged at the detection point D on the instrument 2 and oriented orthogonally to one another and which are used to measure the strength and direction of the magnetic field M at the position of the detection point D. Corresponding measurement values are routed by way of a connecting cable 4 from the instrument 2 to an evaluation unit of the tracking system 3. The evaluation unit uses the measured magnetic field strength to determine the coordinates of the point $p_{TCS}$ in the tracking coordinate system TCS.

The facility 1 further comprises an imaging apparatus in the form of a (C-arm) x-ray device 10. The x-ray device 10 comprises a so-called C-arm 11, the arms of which support an x-ray emitter 12 and an x-ray detector 13 in such a manner that they face one another along an image axis 14. The C-arm 11 can be pivoted in respect of a base 15 about two mutually perpendicular axes, so that the image axis 14 can assume almost any orientations in respect of a three-dimensional spatial coordinate system RCS with coordinates $x_{RCS}$, $y_{RCS}$ and $z_{RCS}$ fixed by the base 15.

In respect of the x-ray device 10 a two-dimensional Cartesian image coordinate system PCS is also defined. The image coordinate system PCS comprises two coordinates $u_{PCS}$ and $v_{PCS}$, which are perpendicular to the image axis 14 and therefore span a plane that is coplanar with a detector area 16 of the x-ray detector 13. In the context of the image coordinate system PCS the position of each image point $p_{PCS}$ of an x-ray image R recorded using the x-ray detector 13 can be determined in units of the coordinates $u_{PCS}$ and $v_{PCS}$.

The facility 1 finally comprises a control unit 20 formed by a data processing system. The control unit 20 is used primarily to activate the x-ray device 10 and to process and evaluate the x-ray images R produced by it. The control unit 20 is connected by way of a data line 21 to the x-ray device 10 for this purpose. The control unit 20 is also connected by way of a data line 22 to a screen 23 to output the x-ray images R.

By recording an x-ray image R it is possible to map and display the instrument 2 as an alternative or in addition to the inside of the body of a patient 25 shown schematically on a patient table 24. Such an x-ray image R of the instrument 2 is shown schematically on the screen 23 in FIG. 1.

Figure 2:
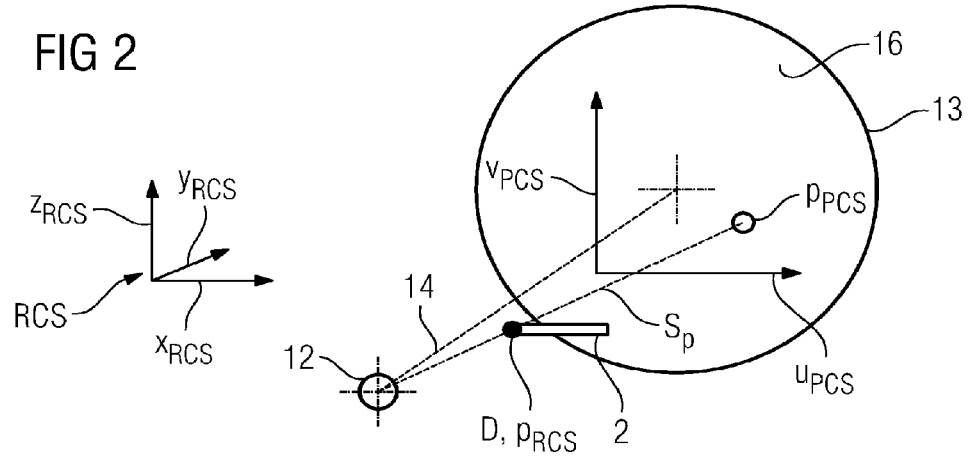
FIG. 2 shows a schematic diagram of a position of the instrument in a spatial coordinate system and in an image coordinate system of the x-ray device.

As can be seen in particular in FIG. 2, when such an x-ray image R is being recorded the detection point D on the instrument 2, which is at a point $p_{RCS}$ in respect of the spatial coordinate system RCS, is projected onto the detector area 15 into one of the image points $p_{PCS}$. The projection line connecting the x-ray emitter 12 to the image point $p_{PCS}$ by way of the point $p_{RCS}$ is shown here as the image beam $s_p$ of the image point $p_{PCS}$.

The mapping of the instrument 2 on the x-ray image R is utilized in the context of the facility 1 to determine the instrument position using the x-ray device 10. A pattern identification algorithm is implemented in the control unit 20 for this purpose, to identify the image of the instrument 2 in the digital x-ray image R and determine the coordinates $u_{PCS}$, $v_{PCS}$ of the image point $p_{PCS}$ corresponding to the detection point D. However because of the two-dimensional nature of the image coordinate system PCS it is not possible to conclude the instrument position in space uniquely in this manner. Instead—as shown in FIG. 2—only the image beam $s_p$, on which the detection point D is located, can be determined based on the coordinates $u_{PCS}$, $v_{PCS}$ and the known orientation of the image axis 14 in respect of the spatial coordinate system RCS.

In order to be able to use the information about the instrument position obtained using the tracking system 3 and the x-ray device 10 in combination, the tracking coordinate system TCS and the image coordinate system PCS are mapped onto one another during the course of a so-called registration. In other words the relative location of the tracking coordinate system TCS to the image coordinate system PCS is determined. A registration module 26 embodied as a software module is implemented in the control unit 20 for this purpose. To carry out registration the control unit 20 also activates the tracking system 3 by way of a data line 27. Measurement values relating to the points $p_{TCS}$ of the instrument position in the tracking coordinate system TCS captured by the tracking system 3 are also supplied to the control unit 3 by way of this data line 27.

With regard to the mapping of the tracking coordinate system TCS onto the image coordinate system PCS a transformation rule in the form of the matrix equation $$p_{PCS} = M_p \cdot T \cdot p_{TCS} \quad \text{EQU 1}$$

is stored in the context of the registration module 26. For simplified mathematical processing the points $p_{PCS}$ and $p_{TCS}$ in EQU 1 are written in the form of so-called homogeneous coordinates and in this context are extended respectively by a (formal) dimension:

$p_{PCS} = (u_{PCS}, v_{PCS})^T \rightarrow p_{PCS} = (u_{PCS}, v_{PCS}, 1)^T$
$p_{TCS} = (x_{TCS}, y_{TCS}, z_{TCS})^T \rightarrow p_{TCS} = (x_{TCS}, y_{TCS}, z_{TCS}, 1)^T$ The so-called transformation matrix T in EQU 1 maps the point $p_{TCS}$ of the tracking coordinate system TCS onto the point $p_{RCS}$ of the spatial coordinate system RCS:

$$p_{RCS} = T \cdot p_{TCS} \quad \text{EQU 2}$$

The transformation matrix T has the dimension 4×4 and thus maximum 16 unknown parameters, whose values are to be determined during the course of registration. The transformation matrix T here allows in particular the formulation of any affine mapping of the tracking coordinate system TCS onto the spatial coordinate system RCS, namely a combination of rotations, translations, scalings and shears.

If the tracking coordinate system TCS is not distorted or is only distorted to a negligible degree in respect of the spatial coordinate system RCS, the mapping produced by the transformation matrix T can be reduced to a rigid mapping with three degrees of freedom of rotation and three degrees of freedom of translation. In this simple instance the translation matrix T has only 6 parameters to be determined independently of one another.

The so-called projection matrix $M_p$ maps the spatial coordinate system RCS onto the image coordinates PCS:

$$p_{PCS} = M_p \cdot p_{RCS} \quad \text{EQU 3}$$

The projection matrix $M_p$ has the dimension 3×4. The projection matrix $M_p$ thus has 12 elements, whose values are determined by the known orientation of the image axis 14 in respect of the spatial coordinate system RCS.

To carry out registration a user (not shown) holds the instrument 2 in a common capture region of the tracking system 3 and the x-ray device 10 and then starts the registration algorithm implemented by the registration module 26.

During the course of this algorithm the registration module 26 prompts the x-ray device 10 to record one x-ray image $R_i$ respectively a number of times at successive times $t_i$ (i=1, 2, ..., n). At the same times $t_i$ the registration module 26 prompts the tracking system 3 to measure one associated point $(p_{TCS})_i$ respectively for the instrument position. The common activation of the x-ray device 10 and the tracking system 3 by the control unit 20 means that image recording and/or position determination respectively take place synchronously. The instrument 2 is moved respectively by the user between times $t_i$. In the case of a hand-held instrument 2 this movement occurs automatically due to the motor activity of the user, therefore unconsciously on the part of the user. It can however also result from the purposeful use of the instrument 2 during medical treatment of the patient 25. Also between times $t_i$ the orientation of the image axis 14 in space can also be changed by pivoting the C-arm 11. The control unit 20 uses the x-ray images $R_i$ respectively to determine the associated image point $(p_{PCS})_i$, onto which the detection point D is projected.

If the distortion of the tracking coordinate system TCS and other measurement errors can be ignored, it is essentially sufficient to record the instrument position at n=3 times $t_i$. The resulting three point pairs $(p_{PCS})_i$ and $(p_{TCS})_i$ can be used to resolve EQU 1 analytically.

To reduce the statistical measurement error however significantly more measurements (n>3) are preferably activated. The registration module 26 then uses the point pairs $(p_{TCS})_i$ and $(p_{PCS})_i$ thus obtained respectively at identical times $t_i$ to resolve EQU 1 in an approximate manner in an iteration method whilst determining the parameters of the transformation matrix T. In this process a predetermined number of degrees of freedom of the transformation matrix T (e.g. 3 rotation directions and 3 translation directions) are changed systematically so that EQU 1 is satisfied in the best possible manner for all recorded point pairs $(p_{TCS})_i$ and $(p_{PCS})_i$. A mean quadratic error of EQU 1 can in particular be minimized as a measure of the satisfaction of EQU 1.

With impedance-based tracking systems in particular measurement errors frequently occur, which result in incorrect determination of the point $p_{TCS}$ to differing degrees as a function of location. Compared with the spatial coordinate system RCS the tracking coordinate system TCS appears distorted as a result, so that the two coordinate systems TCS and RCS can no longer be made satisfactorily congruent by affine mapping. If there is greater distortion of the tracking coordinate system TCS, sufficiently precise resolution of EQU 1 is therefore often not possible.

In this instance the registration module 26 switches to a distortion elimination mode, in the context of which the registration module 26 uses a stored transformation rule of the type $$\Sigma(M(T(p_{TCS}),s_p) + \alpha S(T)) \quad \text{EQU 4}$$

Here $T(p_{TCS})$ is a transformation function, which maps each point $p_{TCS}$ of the tracking coordinate system TCS onto an (in principle any) associated point $p_{RCS}$ of the spatial coordinate system RCS:

$$p_{RCS} = T(p_{TCS}) \quad \text{EQU 5}$$

The function $M(T(p_{TCS}),s_p)$ shows the distance between the point $p_{RCS}$ calculated by way of EQU 5 and the known image beam $s_p$.

S is a measure of the degree of distortion of the tracking coordinate system TCS. In other words S is a measure of the deviation of the mapping function T from a rigid mapping, in other words a mapping determined solely by rotations and translations. The parameter α is a weighting factor that can be determined empirically.

Functions T and S suitable for use in EQU 4 are known for example from B. Fischer, J. Modersitzki, "Intensity based image registration with a guaranteed one-to-one point match", Methods of Information in Medicine, Stuttgart (Schattauer Verlag), 2004, 43:327-330).

The sum Σ in EQU 4 runs over all points $p_{TCS}$ of the tracking coordinate system TCS (quantized appropriately for these purposes).

The registration module 26 parameterizes the transformation function T by minimizing EQU 4 while varying the transformation function T. The registration module 26 uses a predetermined approximate registration as an initial value of the transformation function T for the minimization process. The registration module 26 in particular uses the best resolution of EQU 1 as the approximate registration, it having been possible to determine this before the switch to distortion elimination mode.

What is claimed:

1. A method for calibrating an instrument location apparatus with an imaging apparatus, comprising:

temporally synchronizing the instrument location apparatus with the imaging apparatus by a control unit;

moving a medical instrument relative to a tracking coordinate system of the instrument location apparatus and relative to an image coordinate system of the imaging apparatus;

simultaneously measuring a position of the medical instrument both by the instrument location apparatus and by the imaging apparatus; and parameterizing a transformation rule stored in a registration module for mapping the tracking coordinate system onto the image coordinate system based on the measured position, wherein the transformation rule is performed by the control unit using a matrix equation of $$P_{PCS} = M_p \cdot T \cdot P_{TCS},$$

wherein:

$P_{PCS}$ is an image point corresponding to the position of the medical instrument in coordinate of the image coordinate system, $P_{TCS}$ is the image point corresponding to the position of the medical instrument in coordinate of the tracking coordinate system, T is a transformation matrix mapping the tracking coordinate system onto a spatial coordinate system of the imaging apparatus, and $M_p$ is a projection matrix mapping the spatial coordinate system of the imaging apparatus onto the image coordinate system as a function of a location of an image axis of the imaging apparatus.

2. The method as claimed in claim 1, wherein the transformation rule comprises an affine mapping in combination with a projection.

3. The method as claimed in claim 1, wherein the position of the medical instrument is measured by measuring a position of a detection point on the medical instrument.

4. The method as claimed in claim 1, wherein the position of the medical instrument is measured by measuring a plurality of positions of a plurality of detection points on the medical instrument.

5. The method as claimed in claim 1, wherein the imaging apparatus comprises two image coordinate systems with images axes angled with one another and measures the position of the medical instrument simultaneously in the two image coordinate systems.

6. The method as claimed in claim 1, wherein parameters of the transformation matrix are determined by iteration.

7. The method as claimed in claim 1, wherein parameters of the transformation matrix are determined by a mathematically analytical resolution of the transformation rule.

8. The method as claimed in claim 1, wherein the image coordinate system is two-dimensional and describes an image area perpendicular to an image axis of the imaging apparatus.

9. The method as claimed in claim 8, wherein a plurality of positions of the medical instrument are measured and an orientation of the image axis is changed between the measurements.

10. The method as claimed in claim 1, wherein a non-rigid transformation rule is parameterized in a minimization method to eliminate a distortion of the tracking coordinate system.

11. The method as claimed in claim 10, wherein the transformation rule comprises a function of $$\Sigma M(T(P_{TCS}), S_p) + \alpha \cdot S(T)$$

wherein:

$P_{TCS}$ is an image point corresponding to the position of the medical instrument in coordinate of the tracking coordinate system, T is a transformation function mapping the tracking coordinate system onto a spatial coordinate system of the imaging apparatus, $S_p$ is an image beam assigned to the image point corresponding to the position of the medical instrument in coordinate of the image coordinate system, M is a distance of the image point from the image beam $S_p$, $\alpha$ is a weighting factor, and S is a degree of the distortion.

12. A device for locating a medical instrument, comprising:

an instrument location apparatus;

an imaging apparatus; and a control unit that:

temporally synchronizes the instrument location apparatus with the imaging apparatus, moves a medical instrument relative to a tracking coordinate system of the instrument location apparatus and relative to an image coordinate system of the imaging apparatus, simultaneously measures a position of the medical instrument both by the instrument location apparatus and by the imaging apparatus, and parameterizes a transformation rule stored in a registration module for mapping the tracking coordinate system onto the image coordinate system based on the measured position, wherein the transformation rule is performed by the control unit using a matrix equation of $$P_{PCS} = M_p \cdot T \cdot P_{TCS},$$

wherein:

$P_{PCS}$ is an image point corresponding to the position of the medical instrument in coordinate of the image coordinate system, $P_{TCS}$ is the image point corresponding to the position of the medical instrument in coordinate of the tracking coordinate system, T is a transformation matrix mapping the tracking coordinate system onto a spatial coordinate system of the imaging apparatus, and $M_p$ is a projection matrix mapping the spatial coordinate system of the imaging apparatus onto the image coordinate system as a function of a location of an image axis of the imaging apparatus.

* * * * *